United States Patent [19]

Leiner

[11] Patent Number: 5,684,629
[45] Date of Patent: Nov. 4, 1997

[54] OPTICAL SYSTEM FOR ENDOSCOPE

[75] Inventor: Dennis C. Leiner, Dublin, N.H.

[73] Assignee: Monadnock Optics, Inc., Huntington Valley, Pa.

[21] Appl. No.: 132,009

[22] Filed: Oct. 5, 1993

[51] Int. Cl.$^6$ .............................. G02B 23/00; A61B 1/00
[52] U.S. Cl. ......................... 359/435; 359/362; 359/434
[58] Field of Search ........................ 359/432, 434, 359/435, 362, 715–716, 754, 772, 380–381; 385/117, 119; 128/4, 6

[56] References Cited

U.S. PATENT DOCUMENTS

| | | | |
|---|---|---|---|
| 3,089,484 | 5/1963 | Hett | 128/6 |
| 3,257,902 | 6/1966 | Hopkins | 359/435 |
| 3,297,022 | 1/1967 | Wallace | 128/6 |
| 3,556,085 | 1/1971 | Takahashi | 128/6 |
| 4,025,155 | 5/1977 | Imai | 359/435 |
| 4,036,218 | 7/1977 | Yamashita et al. | 128/4 |
| 4,148,550 | 4/1979 | MacAnally | 359/435 |
| 4,148,551 | 4/1979 | MacAnally | 359/435 |
| 4,168,882 | 9/1979 | Hopkins | 359/434 |
| 4,267,828 | 5/1981 | Matsuo | 128/6 |
| 4,273,110 | 6/1981 | Groux | 128/6 |
| 4,300,812 | 11/1981 | Nakahashi | 359/432 |
| 4,354,730 | 10/1982 | Bel | 359/434 |
| 4,385,810 | 5/1983 | Hamou | 359/381 |
| 4,545,652 | 10/1985 | Hoogland | 359/715 |
| 4,575,195 | 3/1986 | Hoogland | 359/716 |
| 4,664,486 | 5/1987 | Landre et al. | 359/380 |
| 4,676,606 | 6/1987 | Takahashi | 359/754 |
| 4,693,568 | 9/1987 | Takahashi | 359/772 |
| 4,704,007 | 11/1987 | Landre et al. | 359/380 |
| 4,723,843 | 2/1988 | Zobel | 359/435 |
| 4,784,118 | 11/1988 | Fantone et al. | 128/6 |
| 4,919,112 | 4/1990 | Siegmund | 128/4 |
| 4,946,267 | 8/1990 | Hoogland | 359/737 |
| 4,964,710 | 10/1990 | Leiner | 359/434 |
| 4,993,817 | 2/1991 | Hoogland | 359/708 |
| 5,005,960 | 4/1991 | Heimbeck | 359/435 |
| 5,020,893 | 6/1991 | Karst et al. | 359/435 |
| 5,142,410 | 8/1992 | Ono et al. | 359/435 |
| 5,188,092 | 2/1993 | White | 128/4 |
| 5,341,240 | 8/1994 | Broome | 359/435 |
| 5,359,453 | 10/1994 | Ning | 359/435 |
| 5,412,504 | 5/1995 | Leiner et al. | 359/435 |

FOREIGN PATENT DOCUMENTS

| | | |
|---|---|---|
| 3838168 | 10/1988 | Germany . |
| 544422 | 1/1977 | U.S.S.R. . |
| 683721 | 9/1979 | U.S.S.R. . |
| 686725 | 9/1979 | U.S.S.R. . |
| 7218 | 3/1988 | WIPO ............................ 359/434 |

OTHER PUBLICATIONS

Warren J. Smith, Modern Optical Engineering, pp. 159, 160 (1966).

The Handbook of Plastic Optics, 2nd Edition, pp. 56–93 (1983).

Primary Examiner—Thong Nguyen

[57] ABSTRACT

A relay lens system to be incorporated in an endoscopic optical assembly is provided. The relay lens system includes at least one relay lens module for relaying an image between successive image planes. The relay lens module consists of two identical optical assemblies arranged in bilateral symmetrical relation relative to a median plane disposed between the two assemblies. Each optical assembly includes a glass plano cylinder and first and second curved lens components attached to each end of the plano cylinder. The lenses forming the lens components are fabricated from different optical materials including polymeric materials to correct aberrations within the system. The physical and geometrical characteristics of the components are selected to effectively transfer a bright image to the viewer.

33 Claims, 5 Drawing Sheets

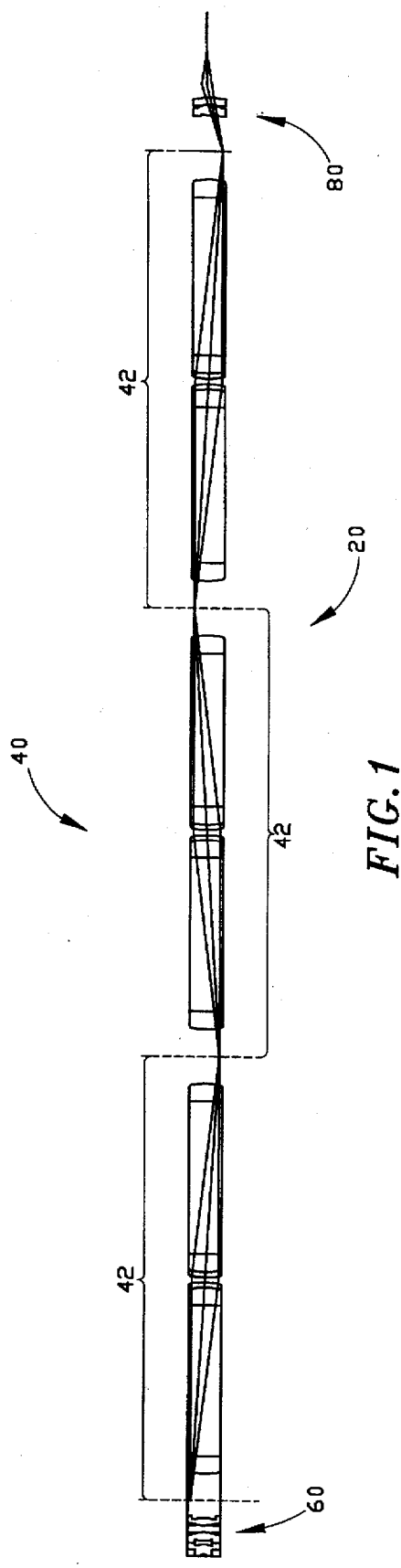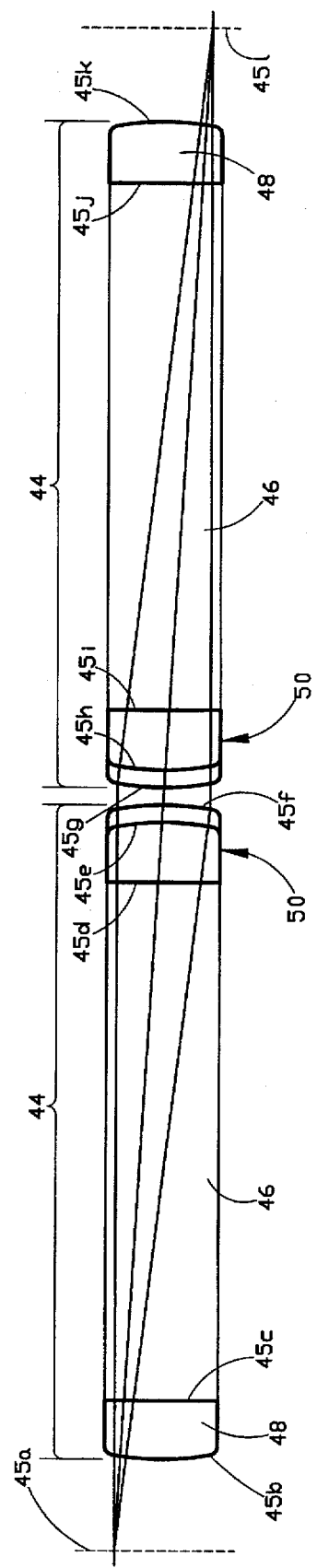

OPTICAL SYSTEM FOR ENDOSCOPE

BACKGROUND OF THE INVENTION

1. Field of the Invention

This invention relates generally to endoscopic optical systems and, in particular, to a relay lens system for a disposable rigid endoscope.

2. Discussion of the Prior Art

Endoscopes are optical instruments which permit the examination of body cavities without the need for extensive surgery. Conventional rigid endoscopes typically include a pipe for illuminating a region of the body cavity to be viewed and an optical lens system mounted in a tube for focusing and relaying the illuminated image from inside the body cavity to the physician. Essential optical components of a conventional lens system include a front combination of lenses constituting the objective lens, a system of relay lenses to carry the image through the scope and an eye lens which produces a magnified virtual image for the viewer. Examples of such optical systems for endoscopes are described in U.S. Pat. Nos. 3,089,484 to Hett, 3,257,902 to Hopkins, 3,556,085 to Takahashi, 4,036,218 to Yamashita, 4,267,828 to Matsuo and 4,273,110 to Groux.

There are several drawbacks in the endoscopes of the prior art, specifically with regard to the complexity and expense of the optical systems incorporated therein. The optical components are typically made of glass that is ground and polished by expensive manufacturing techniques. As a result, the cost of these instruments is relatively high which thereby precludes disposing of the instrument after each surgery. It has become increasingly important to dispose of these instruments after each surgery to eliminate the risk of exposing the next patient to diseases such as AIDS or hepatitis. While most surgical instruments can be sterilized with high pressure steam, the delicate nature of optical systems in endoscopes makes such sterilization difficult. Also, since most of these instruments are inherently fragile, they are frequently broken, at great cost and inconvenience to the user.

In an effort to reduce the cost and complexity of the prior art systems, U.S. Pat. No. 4,784,118 to Fantone describes an endoscope in which the light pipe, and the objective, relay, and viewing lens assemblies are all made of polymeric materials, such as acrylics, polystyrenes, polycarbonates and styrene-acrylonitrile (SAN) copolymers, by conventional injection molding techniques.

Although the Fantone device offers some advantages over prior art optical systems, the device has several drawbacks. The polymeric relay lenses are composed of only one material which increases the chromatic aberration of the image and reduces the resolution. In addition, in order to obtain a bright image, the polymeric lenses have to be manufactured such that the length to diameter ratios of many of the lenses is relatively high. This is very difficult to achieve using currently known manufacturing techniques.

U.S. Pat. No. 4,964,710 to Leiner discloses a unique hybrid relay lens system that overcomes the problems with the Fantone endoscope and the other aforementioned prior art. This relay lens system incorporates glass plano cylinders disposed between molded polymeric curved surface lenses which have a thickness on the same order of magnitude as their diameter. The polymeric lenses are optionally fabricated from two different polymers to facilitate correction of chromatic aberration. In order to achieve a bright image, the plano glass cylinders with flat polished end faces are placed in between the polymeric lenses. In contrast to ground and polished lenses, the plano glass cylinders can be economically made in large quantities, while the smaller polymeric lenses can be economically and accurately made by known injection molding processes.

Despite the teachings of the prior art, it remains desirable to provide an endoscope which is efficient and reliable to manufacture and which provides a brighter image while enhancing resolution. The present invention relates to a device which achieves these objectives by providing an improved relay lens system to be incorporated in a rigid endoscope.

SUMMARY OF THE INVENTION

According to the present invention, a relay lens system using a combination of polished glass and molded polymeric lenses is provided to be incorporated in an endoscope. The relay lens system comprises at least one relay lens module for relaying an image between successive image planes within the endoscope. The relay lens module comprises at least one plano glass cylinder and at least one polymeric lens component axially aligned with the plano glass cylinder and adhered to an end surface thereof.

In a preferred embodiment, the relay lens module comprises two lens assemblies arranged in bilateral symmetrical relation about a median plane disposed between the two assemblies. Each lens assembly comprises a central glass plano cylinder having first and second end surfaces, a first lens component axially aligned with the plano cylinder and positioned adjacent the first end surface thereof and a second lens component axially aligned with the plano cylinder and positioned adjacent the second end surface thereof. At least one of the first and second lens components comprises a polymeric material and is adhered to a respective end surface of the central glass plano cylinder.

The relay lens system of the present invention comprises a plurality of identical lens modules aligned along a common axis within the endoscope. The geometrical and physical characteristics of each module are selected to effectively transfer a bright image of an object to a successive image plane while also allowing for the correction of image aberrations. It is envisioned that the relay lens system can be readily incorporated into conventional endoscopic instrumentation and used in combination with conventional objective lens and eye lens assemblies.

BRIEF DESCRIPTION OF THE DRAWINGS

The accompanying drawings, referred to herein and constituting a part hereof, illustrate preferred embodiments of the present invention and together with the description, serve to explain the principles of the present invention, wherein:

FIG. 1 is an optical schematic of an endoscopic optical system incorporating the relay lens system of the present invention and illustrating ray path and image orientation;

FIG. 2 is an enlarged optical schematic of a single relay lens module of the relay lens system shown in FIG. 1 and illustrates ray path and image orientation within the module.

DETAILED DESCRIPTION OF THE PREFERRED EMBODIMENTS

Figure 3:
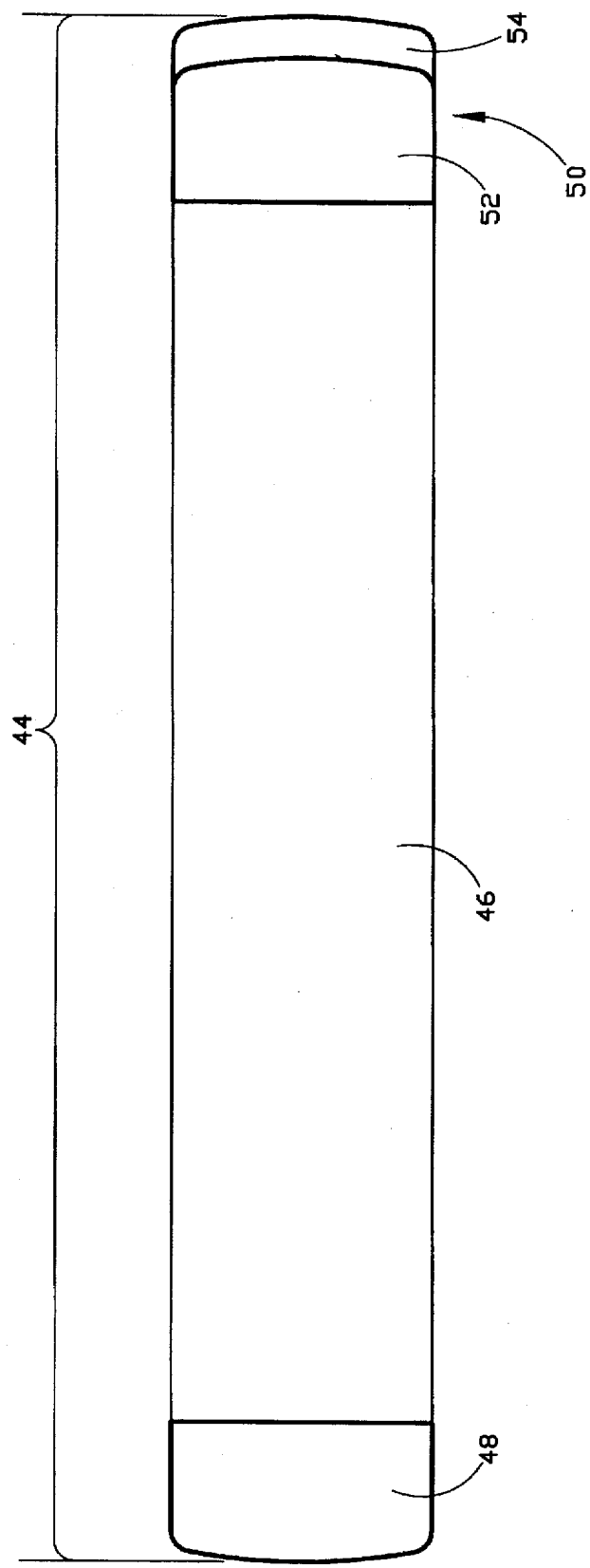
FIG. 3 is an enlarged optical schematic of an optical assembly of the single relay lens module of FIG. 2.

Referring now to the drawings and, in particular, to FIG. 1, there is shown a schematic of an endoscopic optical system 20 incorporating the novel relay lens system 40 of the present invention. Relay lens system 40 finds particular application in disposable endoscopes and can be used in combination with a conventional objective lens assembly 60 and a conventional eye lens assembly 80 as shown.

Relay lens system 40 includes a plurality of relay lens modules 42, arranged in end to end fashion along a common axis. Each module 42 is identical with regard to the optical elements contained therein, and is capable of transferring an image from an image plane at the entrance side of the module to a successive image plane formed on the exit side.

Referring now to FIG. 2, the relay lens module 42 of the present invention is illustrated in detail. Lens module 42 includes two identical optical assemblies 44 arranged in a bilateral symmetrical end to end manner about a median plane equidistantly disposed between the two assemblies. The assemblies 44 are separated by an air gap. Each assembly 44 includes a glass plano cylinder 46 having a polished adjacent end face and a polished outer end face relative to the other component in the module. Glass plano cylinder 46 ensures the transfer of a bright image between the modules. Each assembly 44 further includes single lens 48 and doublet lens 50 bonded to the outer end face and the adjacent end face of plano cylinder 46, respectively.

As best shown in FIG. 3, single lens 48 is preferably a plano-convex lens with the planar surface of the lens being bonded to plano cylinder 46 by conventional adhesive means. A suitable adhesive for this purpose is Norland 68 manufactured by Norland Products Inc. The convex surface of lens 48 may be coated with a broad band anti-reflection coating to reduce reflection losses at the air-lens interface. Single lens 48 is fabricated from a polymeric material, such as an acrylic, polystyrene, polycarbonate, or copolymer styrene-acrylonitrile (SAN). In a preferred embodiment, single lens 48 is fabricated from an acrylic. Single lens 48 may be formed by conventional injection molding techniques, such techniques being capable of forming precise lenses, relatively inexpensively and in large volumes.

Doublet lens 50 consists of two lens elements, specifically, first lens 52 and second lens 54, bonded to each other along adjacent surfaces to form the doublet. Preferably, first lens 52 is a plano-convex lens with the planar surface of the lens 52 being bonded to the adjacent end face of cylinder 46. Second lens 54 is preferably a meniscus (concavo-convex) lens. Doublet 50 is preferably fabricated from two different polymeric materials to allow for the correction of chromatic aberration within the lens system. In a preferred embodiment, lens 52 is formed from an acrylic while lens 54 is formed from either a polycarbonate or polystyrene. It is to be noted that other combinations of optical materials for correcting chromatic aberration would be apparent to one skilled in the art. Lens 52 and 54 may also be manufactured by known injection molding techniques.

In the optical arrangement of lens module 42, single lens 48 functions as a field lens, and as such, bends light ray bundles at the edge of the field, which would otherwise miss doublet lens 50, back toward the longitudinal axis defined by the optical system to thereby minimize vignetting. This is a significant feature of the present invention in that the field of view may be increased without increasing the diameter of doublet 50.

Referring again to FIG. 2, the geometrical characteristics of module 42 are defined by an entrance image plane 45a, a front surface 45b, a first bonded surface 45c, a second bonded surface 45d, a third bonded surface 45e, a first inner surface 45f, a second inner surface 45g, a fourth bonded surface 45h, a fifth bonded surface 45i, a sixth bonded surface 45j, a rear surface 45k and an exit image plane 45l.

The geometrical and optical parameters of module 42 of the relay lens system 40 of the present invention are recorded in Table 1 below. In the Table, surfaces A, B–K and L correspond to image plane 45a, surfaces 45b–45k and exit image plane 45l, respectively.

TABLE 1

| SURFACE | RADIUS | THICKNESS | MEDIUM | INDEX | ABBE NO. |
|---|---|---|---|---|---|
| A | Image Plane | 1.0 ± .03 | Air | 1.000 | |
| B | 13.615 | 3.0 ± .03 | Acrylic | 1.492 | 57.4 |
| C | Plano | 44.0 ± .10 | SF2 | 1.648 | 33.9 |
| D | Plano | 3.0 ± .03 | Acrylic | 1.492 | 57.4 |
| E | −10.860 | 1.0 ± .03 | Polystyrene | 1.590 | 30.9 |
| F | −15.770 | 1.0 ± .03 | Air | 1.000 | |
| G | 15.770 | 1.0 ± .03 | Polystyrene | 1.590 | 30.9 |
| H | 10.860 | 3.0 ± .03 | Acrylic | 1.492 | 57.4 |
| I | Plano | 44.0 ± .10 | SF2 | 1.648 | 33.9 |
| J | Plano | 3.0 ± .03 | Acrylic | 1.492 | 57.4 |
| K | −13.615 | 1.0 ± .03 | Air | 1.000 | |
| L | Image Plane | | | | |

*dimensions are in millimeters

While Table 1 provides a description of a preferred embodiment of the invention, various modifications, alternate construction materials and equivalents may be employed without departing from the spirit of the invention. For example, the size of the air gap between optical components may be altered as well as the radii of curvature of the lenses and type of polymeric lenses incorporated in the optical module.

In a preferred embodiment, the relay lens system comprises three lens modules aligned in end to end fashion along a common axis as shown in FIG. 1. Preferably, the lens modules are interconnected by spacers (not shown). Interconnecting the modules is very desirable in that the relay lens assembly may be assembled as a single unit. This greatly facilitates mounting of the relay lens assembly within the endoscope.

Each module 42 of the relay lens system of the present invention may be secured to a disposable endoscope by conventional methods and, as previously mentioned, may be used in combination with a conventional objective lens assembly 60 and eye lens assembly 80 as shown in FIG. 1 to effectively transfer an image from the object site to the viewer. Preferably, the objective lens and eye lens are fabricated from polymeric materials as well as to further reduce the cost of the endoscope.

Figure 4:
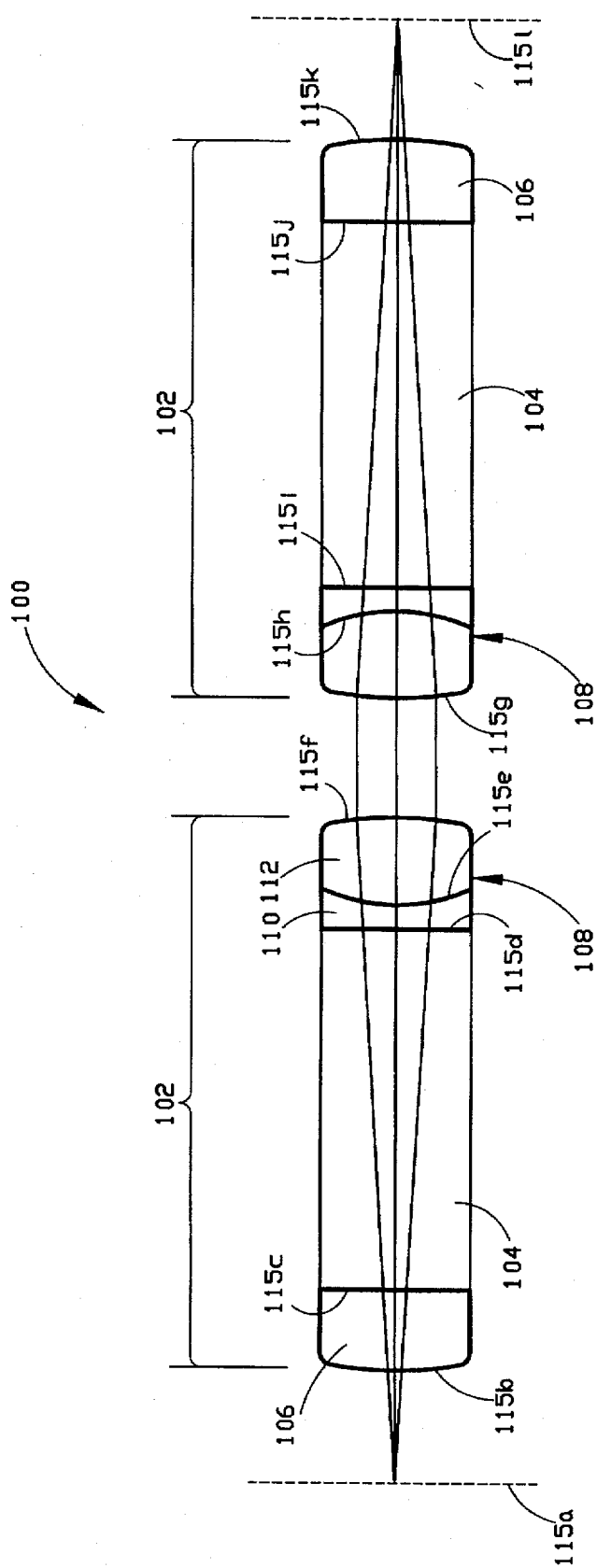
FIG. 4 is an enlarged optical schematic of an alternative single relay lens module to be incorporated in an endoscopic optical system and illustrates ray path and image orientation.

Referring now to FIG. 4 there is illustrated a schematic view of an alternative embodiment of a single relay lens module to be incorporated in an endoscopic optical system. Lens module 100 is substantially similar to the lens module described in connection with the embodiment of FIG. 2 and includes two lens assemblies 102 separated by an air gap.

Each assembly includes a glass plano cylinder 104 having a single plano convex lens 106 affixed to a first end face thereof and a doublet lens 108 affixed to a second end face thereof.

Single plano convex lens 106 may be formed of any suitable optical material. In a preferred embodiment, single lens 106 is formed from acrylic. Single lens 106 may also be formed of any of the aforementioned polymeric materials including polycarbonate, polystyrene and styrene-acrylonitrile (SAN) copolymers.

Doublet lens 108 including first lens element 110 bonded to second lens element 112 may also be formed of any suitable optical material. In a preferred embodiment, first lens element 110 is a plano-concave lens and is fabricated from polystyrene. Second lens element 112 is a double convex lens and is fabricated from acrylic.

The geometrical and optical parameters of this embodiment are recorded in Table 2 below. In the Table, surfaces A, B–K and L correspond to image plane 115a, surfaces 115b–115k and exit image plane 115l, respectively.

TABLE 2

| SUR-FACE | RADIUS | THICKNESS | MEDIUM | INDEX | ABBE NO. |
|---|---|---|---|---|---|
| A | Image Plane | 3.0 ± .03 | Air | 1.000 | |
| B | 7.2000 | 3.0 ± .03 | Acrylic | 1.492 | 57.4 |
| C | Plano | 10.0 ± .10 | F2 | 1.620 | 36.4 |
| D | Plano | 1.0 ± .03 | Polystyrene | 1.590 | 30.9 |
| E | 4.77317 | 3.0 ± .03 | Acrylic | 1.492 | 57.4 |
| F | –8.25904 | 4.0 ± .03 | Air | 1.000 | |
| G | 8.25904 | 3.0 ± .03 | Acrylic | 1.492 | 57.4 |
| H | –4.77317 | 1.0 ± .03 | Polystyrene | 1.590 | 57.4 |
| I | Plano | 10.0 ± .10 | F2 | 1.620 | 36.4 |
| J | Plano | 3.0 ± .03 | Acrylic | 1.492 | 57.4 |
| K | –7.2000 | 3.0 ± .03 | Air | 1.000 | |
| L | Image Plane | | | | |

*dimensions are in millimeters

The above-described embodiments provide an inexpensive relay lens system which furnishes a bright image to the viewer while also minimizing image aberrations. While many relay systems comprise as many as ten elements, there are only four elements in each lens module. The glass plano cylinders can be economically manufactured in large quantities. The polymeric lenses can be made with great precision and with economy of manufacture by known injection molding techniques.

Figure 5:
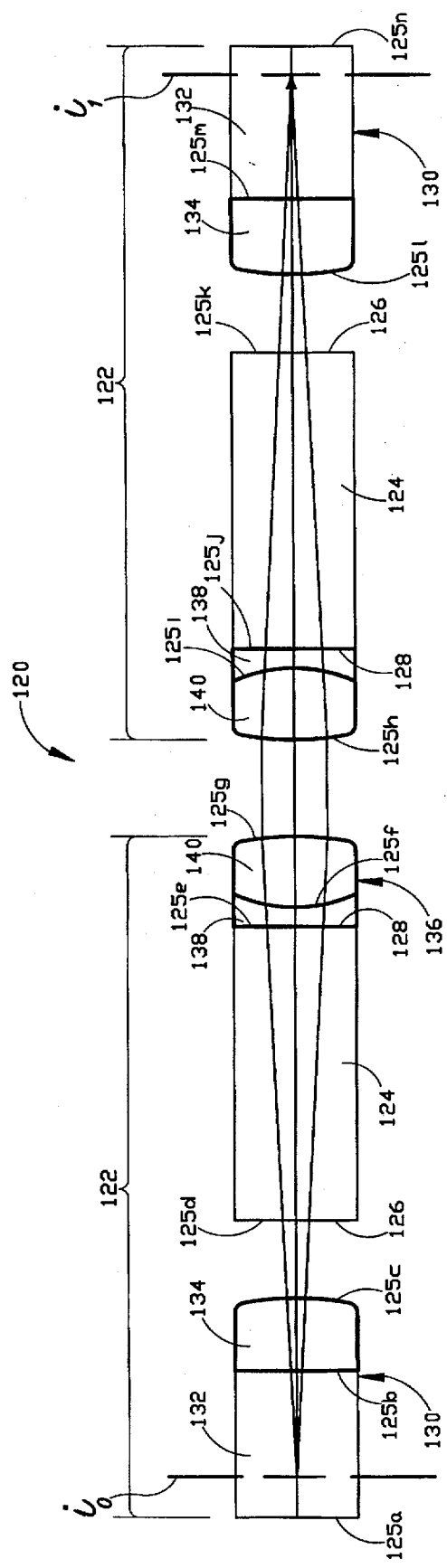
FIG. 5 is an enlarged optical schematic of another alternative single relay lens module to be incorporated in an endoscopic optical system and illustrates ray path and image orientation.

Referring now to FIG. 5 there is illustrated another alternative embodiment of the relay lens system of the present invention. Relay lens module 120 includes two relay lens assemblies 122 arranged in bilateral symmetrical end to end relation relative to a median plane disposed between the two assemblies 122 and separated by an air gap. Each assembly 122 includes a central glass plano cylinder 124 with first and second end surfaces, 126, 128 respectively. Adjacent first end surface 126 of central cylinder 124 is a first optical component 130 including a glass plano cylinder element 132 and a plano-concave lens 134 affixed to one end surface of the cylinder element. In the preferred embodiment, the plano-concave lens 134 is proximate central glass plano cylinder 124 and is separated from the central cylinder by an air gap. Lens 134 is preferably formed from acrylic.

A second optical component 136 is affixed to the second end surface of central cylinder 124. Second lens component 136 is a doublet lens including a plano-concave lens 138 fabricated from polystyrene and a double convex lens 140 fabricated from acyclic.

A significant feature of relay lens module 120 depicted in FIG. 5 is that the images $i_0$, $i_1$ formed by the module 120 are located within glass cylinder 132. Accordingly, in-focus blemishes are reduced as compared to systems in which the images are located near a lens surface.

Referring still to FIG. 5, the geometrical characteristics of module 120 are defined by front surface or entrance image plane 125a, a first bonded surface 125b, a second surface 125c, a third surface 125d, a fourth bonded surface 125e, a fifth bonded surface 125f, a sixth surface 125g, a seventh surface 125h, an eighth bonded surface 125i, a ninth bonded surface 125j, a tenth surface 125k, an eleventh surface 125l, a twelfth bonded surface 125m and a rear surface or exit image plan 125n.

The geometrical and optical parameters of this embodiment of the module are recorded in Table 3 below.

TABLE 3

| SUR-FACE | RADIUS | THICKNESS | MEDIUM | INDEX | ABBE NO. |
|---|---|---|---|---|---|
| A | Plano | 5.0 ± .03 | F2 | 1.620 | 36.4 |
| B | Plano | 3.0 ± .03 | Acrylic | 1.492 | 57.4 |
| C | –25.000 | 3.0 ± .03 | Air | 1.000 | |
| D | Plano | 10.0 ± .10 | F2 | 1.620 | 36.4 |
| E | Plano | 1.0 ± .03 | Polystyrene | 1.590 | 30.9 |
| F | 7.000 | 3.0 ± .03 | Acrylic | 1.492 | 57.4 |
| G | –8.000 | 6.0 ± .03 | Air | 1.000 | |
| H | 8.000 | 3.0 ± .03 | Acrylic | 1.492 | 57.4 |
| I | –7.000 | 1.0 ± .03 | NOR61 | 1.590 | 30.9 |
| J | Plano | 10.0 ± .10 | F2 | 1.620 | 36.4 |
| K | Plano | 3.0 ± .03 | Air | 1.000 | |
| L | 25.000 | 3.0 ± .03 | Acrylic | 1.492 | 57.4 |
| M | Plano | 5.0 ± .03 | F2 | 1.620 | 36.4 |
| N | Plano | | | | |

*dimensions are in millimeters

The embodiment depicted in FIG. 5 shows only one relay lens module 120, but, as would be readily apparent to one skilled in the art, a practical endoscope may consist of several relay pairs. For example, an endoscope would typically consist of three lens modules 120. Further, the thickness of plano cylinder 132 may be twice the thickness shown in FIG. 5 since adjacent lens modules would be present in the optical system. In addition, an endoscope would also contain an objective lens system located distal to the relay lenses to provide a wide field of view and an eye lens system for magnifying the most proximal image coming out of the relay lens system.

The relay lens systems of the above-described embodiments are each highly effective in transferring an illuminated image of an object to the viewer. In particular, each lens system produces exceptional results with regard to modulation transfer function (MTF), which is a useful parameter in evaluating the optical quality or performance of an image forming system. MTF also referred to as frequency response, sine-wave response or contrast transfer, is commonly defined as the ratio of the modulation in the image to that in the object as a function of the frequency (cycles per unit angle or length) of the sine-wave distribution pattern. A plot of modulation against frequency (angular frequency of the bars expressed as so many lines per degree in the image space) is an applicable measure of the performance of an imaging system. It should be noted that, for a given lens, the plot of MTF differs by wavelength, by field obliquity, by orientation of the bars, and from point to point along the lens axis.

Figure 6:
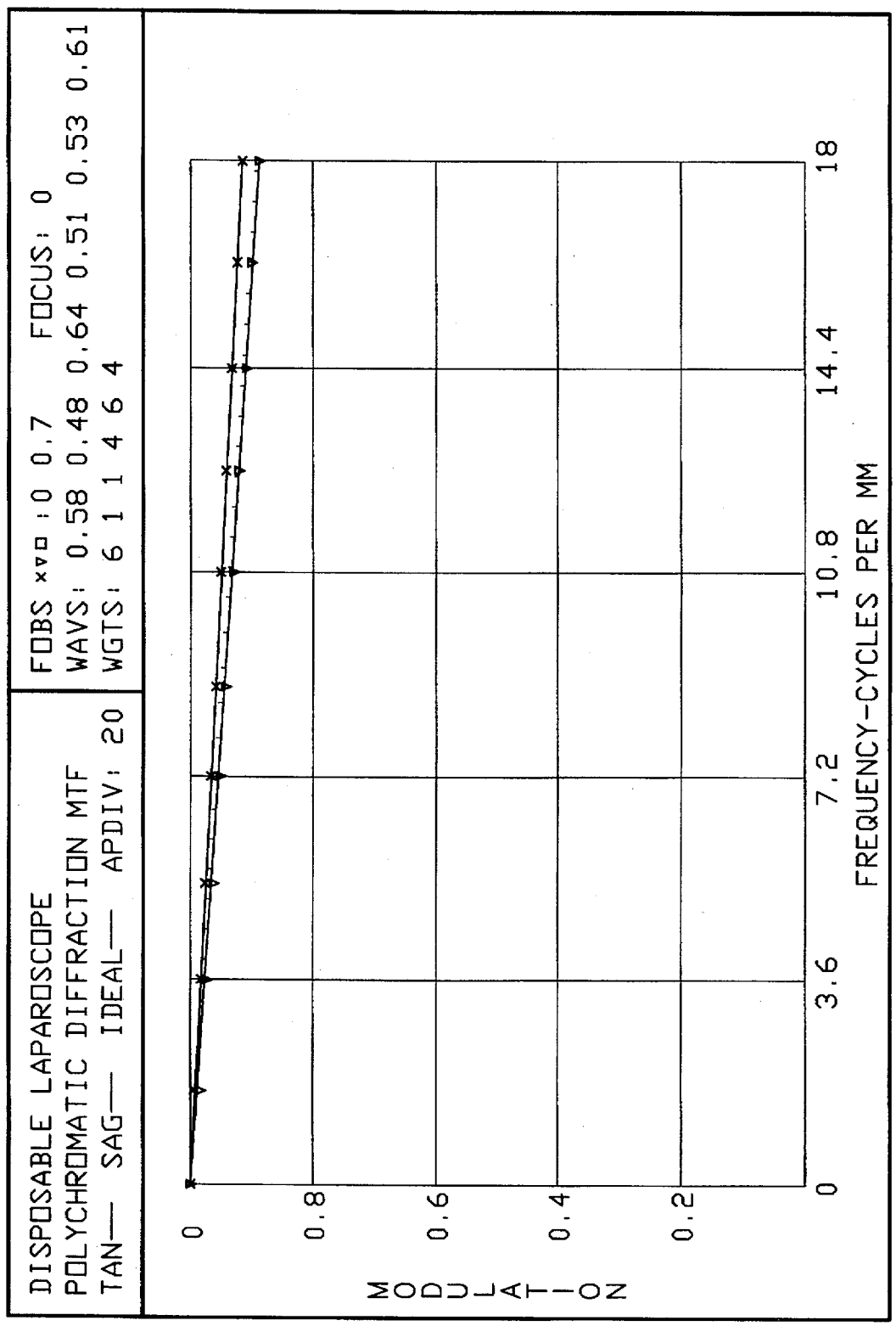
FIG. 6 is a general graphic representation of modulation transfer function (MTF) curves for the above embodiments of the relay lens systems.

FIG. 6 is a graph depicting MTF curves for the relay lens systems described above. MTF values were calculated along the lens axis and for points off the axis at 70% of the maximum angular field of view. As illustrated in the graph, the system has high modulation at the low spatial frequencies as well as the higher spatial frequencies for these points. Specifically, the modulation for the spatial frequencies ranging from 0 cycles/degree to 6 cycles/degree remains above 0.9 for points along the lens axis and for points off the axis at 70% of the maximum angular field of view. These modulation values are favorable when compared to conventional glass relay lens systems and indicate that the present lens system has theoretical optical resolution comparable to conventional glass relay lens systems.

To the extent not already indicated, it also will be understood by those of ordinary skill in the art that any one of various specific embodiments herein described and illustrated may be further modified to incorporate features shown in other of the specific embodiments.

The invention in its broader aspects therefor is not limited to the specific embodiments herein shown and described but departures may be made therefrom within the scope of the accompanying claims without departing from the principals of the invention and without sacrificing its chief advantages.

What is claimed is:

1. A relay lens system to be incorporated in an endoscopic optical assembly, said relay lens system comprising at least one relay lens module for relaying an image between successive image planes, said lens module comprising two lens assemblies arranged in bilateral symmetrical relation about a median plane disposed between said two assemblies, each said lens assembly including:

a central glass plano cylinder having first and second end surfaces;

a first lens component axially aligned with said plano cylinder and positioned adjacent first end surface;

a second lens component axially aligned with said plano cylinder and positioned adjacent said second end surface; and at least one of said first and second lens components including a polymeric material and being adhered to a respective end surface of said central glass plano cylinders said first and second lens components having different geometrical and optical characteristics.

2. The relay lens system of claim 1, wherein said first lens component comprises a polymeric material selected from the group consisting of acrylics, polystyrenes, polycarbonates and styrene-acrylonitrile (SAN) copolymers.

3. The relay lens system of claim 2, wherein said first lens component is adhered to said first end surface of said central glass plano cylinder.

4. The relay lens system of claim 3, wherein said first lens component comprises a single curved lens.

5. The relay lens system of claim 1, wherein said second lens component comprises a polymeric material selected from the group consisting of acrylics, polystyrenes, polycarbonates and styrene-acrylonitrile (SAN) copolymers.

6. The relay lens system of claim 5, wherein said second lens component is adhered to said second end surface of said glass plano cylinder.

7. The relay lens system of claim 5, wherein said second lens component comprises a doublet lens having a first lens element fabricated from a first optical material and a second lens element fabricated from a second optical material wherein said first and second optical materials are different.

8. The relay lens system of claim 1, wherein said lens assemblies in said lens module are separated by an air gap.

9. A relay lens system to be incorporated in an endoscopic optical assembly, said relay lens system comprising at least one relay lens module for relaying an image between successive image planes, said lens module comprising two lens assemblies arranged in bilateral symmetrical relation about a median plane disposed between said two assemblies, each said lens assembly including:

a central glass plano cylinder having first and second end surfaces;

a first lens component axially aligned with said central plano cylinder and positioned adjacent said first end surface, said first lens component including a glass plano cylinder and a single curved lens;

a second lens component axially aligned with said central plano cylinder and positioned adjacent said second end surface; and wherein an image plane formed by said lens module is disposed within said glass plano cylinder of said first lens component.

10. The relay lens system of claim 9, wherein said single lens of said first lens component is fabricated from a polymeric material selected from the group consisting of acrylics, polystyrenes, polycarbonates and styrene-acrylonitrile (SAN) copolymers.

11. The relay lens system of claim 10, wherein said single lens of said first lens component is adhered to an end surface of said glass plano cylinder of said first lens component.

12. The relay lens system of claim 11, wherein said first lens component and said central glass plano cylinder are separated by an air gap.

13. A relay lens system to be incorporated in an endoscopic optical assembly, said relay lens system comprising at least one relay lens module for transferring an image between successive image planes, said lens module including two lens assemblies arranged in bilateral symmetrical relation about a median plane disposed between said two assemblies, each said lens assembly comprising:

a glass plano cylinder element having first and second end surfaces;

a curved single lens axially aligned with said plano cylinder and affixed to said first end surface; and a curved doublet lens axially aligned with said plano cylinder and affixed to said second end surface, said doublet lens comprising a first lens fabricated from a first material and a second lens fabricated from a second material wherein said first and second materials are different.

14. The relay lens system of claim 13, wherein said single lens is fabricated from a polymeric material selected from the group consisting of acrylics, polystyrenes, polycarbonates and styrene-acrylonitrile (SAN) copolymers.

15. The relay lens system of claim 13, wherein said first material of said doublet lens is a polymeric material selected from the group consisting of acrylics, polystyrenes, polycarbonates and styrene-acrylonitrile (SAN) copolymers.

16. The relay lens system of claim 13, wherein said second material of said doublet is a polymeric material selected from the group consisting of acrylics, polystyrenes, polycarbonates and styrene-acrylonitrile (SAN) copolymers.

17. The relay lens system of claim 13, characterized by the following data:

| SUR-FACE | RADIUS | THICKNESS | MEDIUM | INDEX | ABBE NO. |
|---|---|---|---|---|---|
| A | Image Plane | 1.0 ± .03 | Air | 1.000 | |
| B | 13.615 | 3.0 ± .03 | Acrylic | 1.492 | 57.4 |
| C | Plano | 44.0 ± .10 | SF2 | 1.648 | 33.9 |
| D | Plano | 3.0 ± .03 | Acrylic | 1.492 | 57.4 |
| E | −10.860 | 1.0 ± .03 | Polystyrene | 1.590 | 30.9 |
| F | −15.770 | 1.0 ± .03 | Air | 1.000 | |
| G | 15.770 | 1.0 ± .03 | Polystyrene | 1.590 | 30.9 |
| H | 10.860 | 3.0 ± .03 | Acrylic | 1.492 | 57.4 |
| I | Plano | 44.0 ± .10 | SF2 | 1.648 | 33.9 |
| J | Plano | 3.0 ± .03 | Acrylic | 1.492 | 57.4 |
| K | −13.615 | 1.0 ± .03 | Air | 1.000 | |
| L | Image Plane | | | | |

*dimensions are in millimeters

18. A relay lens system to be incorporated in an endoscopic optical assembly, said relay lens system comprising at least one relay lens module for transferring an image between successive image planes, said lens module comprising two lens assemblies arranged in bilateral symmetrical relation about a median plane disposed between said two assemblies, each said lens assembly comprising:

a glass plano cylinder element having a first and second end surfaces;

a curved single lens axially aligned with said plano cylinder and affixed to said first end surface; and a curved doublet lens axially aligned with said plano cylinder and affixed to said second end surface, said doublet lens comprising a first lens fabricated from a first material and a second lens fabricated from a second material wherein said first and second materials are different wherein said relay lens system is characterized by the following data:

| SUR-FACE | RADIUS | THICKNESS | MEDIUM | INDEX | ABBE NO. |
|---|---|---|---|---|---|
| A | Image Plane | 3.0 ± .03 | Air | 1.000 | |
| B | 7.20000 | 3.0 ± .03 | Acrylic | 1.492 | 57.4 |
| C | Plano | 10.0 ± .10 | F2 | 1.620 | 36.4 |
| D | Plano | 1.0 ± .03 | Polystyrene | 1.590 | 30.9 |
| E | 4.77317 | 3.0 ± .03 | Acrylic | 1.492 | 57.4 |
| F | −8.25904 | 4.0 ± .03 | Air | 1.000 | |
| G | 8.25904 | 3.0 ± .03 | Acrylic | 1.492 | 57.4 |
| H | −4.77317 | 1.0 ± .03 | Polystyrene | 1.590 | 30.9 |
| I | Plano | 10.0 ± .10 | F2 | 1.620 | 36.4 |
| J | Plano | 3.0 ± .03 | Acrylic | 1.492 | 57.4 |
| K | −7.2000 | 3.0 ± .03 | Air | 1.000 | |
| L | Image Plane | | | | |

*dimensions are in millimeters

19. A relay lens system to be incorporated in an endoscopic optical assembly, said relay lens system comprising at least one relay lens module for transferring an image between successive image planes, said lens modules comprising two lens assemblies arranged in bilateral symmetrical relation about a median plane disposed between said two assemblies, each said lens assembly having:

a central glass plano cylinder element having first and second end surfaces;

a first lens component axially aligned with said central glass plano cylinder and positioned adjacent said first end surface thereof, said first lens component including a glass plano cylinder element and a single curved lens affixed to said glass plano cylinder element; and a second lens component including a curved doublet lens axially aligned with said central plano cylinder and affixed to said second end surface thereof, said doublet lens including a first lens fabricated from a first optical material and a second lens fabricated from a second optical material wherein said first and second optical materials are different.

20. The relay lens system of claim 19, wherein at least one of said first and second optical materials of said doublet lens is a polymeric material selected from the group consisting of acrylics, polystyrenes, polycarbonates and styrene-acrylonitrile (SAN) copolymers.

21. The relay lens system of claim 19, wherein said single curved lens of said first lens component is fabricated from a polymeric material selected from the group consisting of acrylics, polystyrenes, polycarbonates and styrene-acrylonitrile (SAN) copolymers.

22. The relay lens system of claim 19, wherein said glass plano cylinder element of said first lens component and said single curved lens of said first lens component are fabricated from different optical materials.

23. The relay lens system of claim 19, wherein said image planes formed by each said lens module are disposed within said glass plano cylinder element of said first lens component.

24. The relay lens system of claim 19, wherein said first lens component and said central glass plano cylinder are separated by an air gap.

25. The relay lens system of claim 19 wherein an image plane formed by said lens module is disposed within said glass cylinder of said first lens component.

26. A relay lens system to be incorporated in an endoscopic optical assembly, said relay lens system comprising at least one relay lens module for transferring an image between successive image planes, said lens modules comprising two lens assemblies arranged in bilateral symmetrical relation about a median plane disposed between said two assemblies, each said lens assembly having:

a central glass plano cylinder element having first and second end surfaces;

a first lens component axially aligned with said central glass plano cylinder and positioned adjacent said first end surface thereof, said first lens component including a glass plano cylinder element and a single curved lens affixed to said glass plano cylinder element; and a second lens component comprising a curved doublet lens axially aligned with said central plano cylinder and affixed to said second end surface thereof, said doublet lens comprising a first lens fabricated from a first optical material and a second lens fabricated from a second optical material wherein said first and second optical materials are different and wherein an image plane formed by said lens module is disposed within said glass cylinder of said first lens component;

wherein said relay lens module is characterized by the following data:

| SUR-FACE | RADIUS | THICKNESS | MEDIUM | INDEX | ABBE NO. |
|---|---|---|---|---|---|
| A | Plano | 5.0 ± .03 | F2 | 1.620 | 36.4 |
| B | Plano | 3.0 ± .03 | Acrylic | 1.492 | 57.4 |
| C | −25.0000 | 3.0 ± .03 | Air | 1.000 | |
| D | Plano | 10.0 ± .03 | F2 | 1.620 | 36.4 |
| E | Plano | 1.0 ± .03 | Polystyrene | 1.590 | 30.9 |
| F | 7.0000 | 3.0 ± .03 | Acrylic | 1.492 | 57.4 |
| G | −8.000 | 6.0 ± .03 | Air | 1.000 | |
| H | 8.000 | 3.0 ± .03 | Acrylic | 1.492 | 57.4 |

-continued

| SUR-FACE | RADIUS | THICKNESS | MEDIUM | INDEX | ABBE NO. |
|---|---|---|---|---|---|
| I | −7.000 | 1.0 ± .03 | Polystyrene | 1.590 | 30.9 |
| J | Plano | 10.0 ± .10 | F2 | 1.620 | 36.4 |
| K | Plano | 3.0 ± .03 | Air | 1.000 | |
| L | 25.000 | 3.0 ± .03 | Acrylic | 1.492 | 57.4 |
| M | Plano | 5.0 ± .03 | F2 | 1.620 | 36.4 |
| N | Plano | | | | |

*dimensions are in millimeters

27. An optical system for a rigid endoscope comprising:
objective lens means for producing an image of an object at a first image plane;
a relay lens system comprising at least one relay lens module for transferring an image between successive image planes, said lens module comprising two lens assemblies arranged in bilateral symmetrical relation relative to a median plane disposed between said two assemblies, each said lens assembly comprising:
a glass plano cylinder element having first and second end surfaces;
a first polymeric curved lens axially aligned with said plano cylinder and positioned adjacent said first end surface; and
a second polymeric curved lens axially aligned with said plano cylinder and positioned adjacent said second end surface; and
eye lens means for viewing an image formed at an exit image plane;
wherein said optical system has a modulation for the spatial frequencies ranging from 0 cycles/degree to 6 cycles/degree remaining above 0.9 for points along the lens axis and for points off said axis at 70% of the maximum angular field of view.

28. The optical system of claim 27, wherein said first polymeric lens comprise a single curved lens.

29. The optical system of claim 28, wherein said second polymeric lens comprises a doublet lens.

30. The optical system of claim 29, wherein said curved lens of said relay lens system comprises a polymeric material selected from the group consisting of acrylics, polystyrenes, polycarbonates and styrene-acrylonitrile copolymers.

31. The optical system of claim 30, wherein said doublet lens comprises a first lens fabricated from a first polymeric material and a second lens fabricated from a second polymeric material wherein said first and second materials are different.

32. The optical system of claim 31, wherein said first material of said doublet lens is a polymeric material selected from the group consisting of acrylics, polystyrenes, polycarbonates and styrene-acrylonitrile copolymers.

33. The optical system of claim 32, wherein said second material of said doublet lens is a polymeric material selected from the group consisting of acrylics, polystyrenes, polycarbonates and styrene-acrylonitrile copolymers.

\* \* \* \* \*